United States Patent [19]

Barnett et al.

[11] Patent Number: 5,235,053

[45] Date of Patent: Aug. 10, 1993

[54] PROCESS FOR THE SYNTHESIS OF 4-HYDROXY-5-HALOPYRROLD[2,3-D]PYRIMIDINE INTERMEDIATES

[75] Inventors: Charles J. Barnett, Indianapolis; Michael E. Kobierski, Greenwood, both of Ind.

[73] Assignee: Eli Lilly and Company, Indianapolis, Ind.

[21] Appl. No.: 902,116

[22] Filed: Jun. 22, 1992

[51] Int. Cl.$^5$ .................... C07D 487/04; C07B 39/00; C07F 7/18
[52] U.S. Cl. ...................................... 544/280; 544/229
[58] Field of Search ......................................... 544/280

[56] References Cited

U.S. PATENT DOCUMENTS 4,996,206  2/1991  Taylor et al. ........................ 514/258

OTHER PUBLICATIONS

Seela, Chem. Ber 111, 2925 (1978).
Cocuzza, A. J., *Tetrahedron Letters*, 29:4061–4064 (1988).
Gerster, et al., *J. Het. Chem.*, 6:207–213 (1969).
Noell, et al., *J. Het. Chem.*, 1:34–41 (1964).

*Primary Examiner*—Mark L. Berch
*Attorney, Agent, or Firm*—Steven A. Fontana; Leroy Whitaker

[57] ABSTRACT

4-Hydroxypyrrolo[2,3-d]pyrimidines are regiospecifically halogenated at the C-5 position by silylation in the presence of an inert organic solvent and iodination, bromination or chlorination.

19 Claims, No Drawings

PROCESS FOR THE SYNTHESIS OF 4-HYDROXY-5-HALOPYRROLO[2,3-D]PYRIMIDINE INTERMEDIATES

FIELD OF THE INVENTION

This invention relates to the fields of pharmaceutical and organic chemistry, and provides processes for the synthesis of 4-hydroxy-5-halopyrrolo[2,3-d]-pyrimidines which are useful, inter alia, as intermediates in the synthesis of a series of complex antimetabolites of the antifolate type.

BACKGROUND OF THE INVENTION

Antimetabolites have been used for a number of years as chemotherapeutic agents in the treatment of cancer. One such drug, methotrexate, is now one of the most widely used anticancer drugs; and many other compounds in the folic acid family have been synthesized, tested and discussed in the chemical and medical literature. The compounds have various activities at the enzymatic level; they inhibit such enzymes as dihydrofolate reductase, folate polyglutamate synthetase, glycinamide ribonucleotide formyltransferase and thymidylate synthetase.

More recently, a series of 4-hydroxypyrrolo[2,3-d]pyrimidine-L-glutamic acid derivatives have been disclosed and shown to be particularly useful antifolate drugs. See, for example, U.S. Pat. Nos. 4,996,206; 5,028,608; 5,106,974; and 4,997,838. In the synthesis of these compounds, an important group of intermediates, 4-hydroxy-5-halo-pyrrolo[2,3-d]pyrimidine derivatives, are frequently synthesized and then reacted with the desired carboxylic acid derivative or L-glutamic acid derivative via conventional techniques.

However, the preparation of 4-hydroxy-5-halopyrrolo[2,3-d]pyrimidines by direct halogenation at the C-5 position of the corresponding 4-hydroxypyrrolo[2,3-d]pyrimidines has not been synthetically useful either because of poor regioselectivity, where halogenation frequently occurs at both the C-5 and C-6 positions, or because of the inconvenience of harsh, multi-step processes. See, for example, Cocuzza, A. J., *Tetrahedron Letters*, 29: 4061-4064 (1988); Gerster, et al., *J. Het. Chem.* 207-213 (1969); and U.S. Pat. No. 4,996,206. The present invention provides an improved process for direct halogenation of 4-hydroxypyrrolo[2,3-d]pyrimidines at the C-5 position.

The resulting compounds, 4-hydroxy-5-halopyrrolo[2,3-d]pyrimidines, are primarily useful as intermediates for the synthesis of antineoplastic glutamic acid derivatives. However, one of ordinary skill in the organic chemical arts will recognize that the usefulness of the intermediates synthesized by the processes of this invention is not limited to the synthesis of the above-described antineoplastic agents.

SUMMARY OF THE INVENTION

The present invention provides a method for preparing 4-hydroxy-5-halopyrrolo[2,3-d]pyrimidines of formula I:

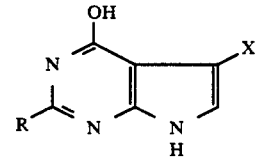

wherein
R is H, $C_1$-$C_4$ alkyl, $C_1$-$C_4$ alkoxy, aryl, benzyl, or a substituent of the formula $R^1$—NH—;
$R^1$ is an amino protecting group; and
X is bromo, chloro or iodo, which comprises
(a) reacting a silylating agent with a 4-hydroxypyrrolo[2,3-d]pyrimidine of formula II

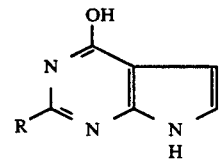

wherein
R is as defined above, in the presence of an inert organic solvent; and
(b) iodinating, brominating or chlorinating the reaction product from step (a).

DETAILED DESCRIPTION OF THE INVENTION

The present invention pertains to processes for the synthesis of 4-hydroxy-5-halopyrrolo[2,3-d]intermediates which are useful, as intermediates in the synthesis of a series of complex antimetabolites of the antifolate type.

The compounds of formula I and II exist in tautomeric equilibrium with the corresponding 4(3H)-oxo compounds. For illustrative purposes, the equilibrium for formula II is shown below, in addition to the pyrrolo[2,3-d]pyrimidine ring system which is numbered as follows:

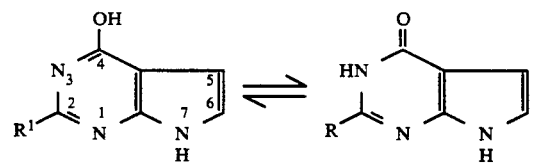

For convenience, the 4-hydroxy form is depicted for formulas I and II, and the corresponding nomenclature is used throughout this specification. However, it is understood that such depictions include the corresponding tautomeric 4(3H)-oxo forms.

The following definitions refer to the various terms used above and throughout the disclosure.

The term "halo" refers to bromo, chloro, fluoro and iodo.

The term "$C_1$-$C_4$ alkyl" refers to the straight or branched aliphatic chains of 1-4 carbon atoms, including methyl, ethyl, propyl, isopropyl, n-butyl, isobutyl, secbutyl and tert-butyl.

The term "$C_1$-$C_4$ alkoxy" represents an alkyl group of 1 to 4 carbon atoms attached through an oxygen bridge such as methoxy, ethoxy, n-propoxy, isopropoxy, and the like.

The term "aryl" denotes an unsubstituted or substituted aromatic residue derived by the removal of a hydrogen atom from an aromatic hydrocarbon, such as, for example, phenyl, thienyl, pyridyl or furyl. The aromatic residues are unsubstituted or substituted with 1, 2 or 3 substituents independently selected from halo, $C_1$–$C_4$ alkyl and $C_1$–$C_4$ alkoxy.

The amino protecting group designated $R^1$ in formulas I and II, and as utilized herein, denotes a group which generally is not found in a final therapeutic compound, but which is intentionally introduced during a portion of the synthetic process to protect an amino group which may otherwise react in the course of chemical manipulations, and is then removed at a late stage of the synthesis. Numerous reactions for the formation and removal of such a protecting group are described in a number of standard works including, for example, "Protective Groups in Organic Chemistry", Plenum Press, (London and New York, 1973); Greene, Th. W., "Protecting Groups in Organic Synthesis", Wiley, (New York, 1981); and "The Peptides", Vol. I, Schroöder and Lubke, Academic Press, (London and New York, 1965).

Typically, an amide utilizing an acyl group which is selectively removable under mild conditions, such as for example, a formyl group, a lower alkanoyl group of from 2 to 8 carbon atoms which is substituted at the 1-position, such as trifluoroacetyl, are useful. A tertiary alkanoyl such as 2,2-dimethylpropionyl is especially useful. Other amino protecting groups include N-alkoxycarbonyls such as N-methoxycarbonyl, N-ethoxycarbonyl, N-(t-butyloxycarbonyl) and N-diisopropylmethoxycarbonyl.

The term "lower alkanoyl group of from 1 to 8 carbon atoms" refers to straight or branched univalent aliphatic acyl groups of 1-8 carbon atoms including, for example, formyl, acetyl, propionyl, butyryl, α-methylpropionyl, valeryl, α-methylbutyryl, β-methylbutyryl, pivaloyl, octanoyl, and the like.

Formula II compounds are prepared by methods commonly known to organic chemists. For example, Davoll, J. (*J. Chem. Soc.*, 131 (1960)) describes the synthesis of 4-hydroxypyrrolo[2,3-d]pyrimidine. In addition, the synthesis of 2-methyl-, 2-ethyl-, n-propyl- and 2-phenyl-4-hydroxypyrrolo[2,3-d]pyrimidines is described by West, R. A., et al., *J. Org. Chem.*, 26: 3809–3812 (1961). Alternatively, the 2-position of the pyrrolo[2,3-d]pyrimidine ring can carry other aryl groups such as thienyl, pyridyl and furyl. In addition to phenyl, each of these aryl groups may be substituted by conventional means known in the art with 1, 2 or 3 substituents independently selected from halo, $C_1$–$C_4$ alkyl and $C_1$–$C_4$ alkoxy.

Preferred formula II compounds include unsubstituted 4-hydroxypyrrolo[2,3-d]pyrimidine and 2-methyl-, 2-ethyl-, 2-methoxy- and 2-phenyl-4-hydroxypyrrolo[2,3-d]pyrimidines.

Other preferred formula II compounds include 2-protected-amino-4-hydroxypyrrolo[2,3-d]pyrimidines. Example 1, infra, describes the preferred method for the synthesis of 2-amino-4-hydroxypyrrolo[2,3-d]pyrimidines while Example 2, infra, describes a representative method for protecting the 2-amino-substituent. Although amino protecting groups generally known in the art would adequately protect the 2-amino-substituent of formula II, an unsubstituted or substituted lower alkanoyl group of 1-8 carbon atoms is preferred. Of these, 2,2-dimethylpropionyl is especially preferred.

The process of this invention is carried out by (a) reacting a silylating agent with a 4-hydroxypyrrolo[2,3-d]pyrimidine of formula II, in the presence of an inert solvent; and (b) iodinating or brominating the resulting product from step (a). This process may be carried out as two independent processes or, preferably, carried out, in situ, as a single process wherein step (b) is conducted immediately following the completion of step (a).

In step (a), generally known silylating agents are employed. See, for example, Calvin, E. W., "Silicon Reagents in Organic Synthesis", Academic Press, (London, et al., 1988) which is herein incorporated by reference. Particularly useful silylating agents include "tri-lower alkyl silyl" agents, the term of which contemplates tri-isopropylsilyl, tri-methylsilyl and tri-ethylsilyl, trimethylsilyl halides, silylated ureas such as bis(trimethylsilyl)urea (BSU), and silated amides such as bis(trimethylsilyl)acetamide (BSA). Of these, BSA is preferred.

In general, the addition of at least 1 molar equivalent of silylating agent to a formula II compound, in the presence of an inert organic solvent, is sufficient to drive the step (a) reaction. However, it is advisable to use at least 2 molar equivalents of silylating agent per mole of substrate to optimize the silylation of formula II compounds. Suitable solvents for this reaction are tetrahydrofuran (THF) and, especially, dimethylformide (DMF). It is preferable to operate step (a) of this process at a temperature in a range from about 25° to about 60° C. However, the optimum operating temperature for a given reaction is easily found according to the routine skill of organic chemists.

When bis(trimethylsilyl)acetamide is employed as the silylating agent, the reaction product is presumably a pyrrolo[2,3-d]pyrimidine of the formula

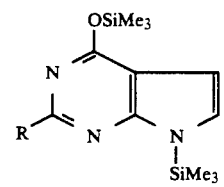

wherein R is as defined above.

Compounds of formula I are then formed by brominating, chlorinating or iodinating the reaction product from step (a). Ideally, step (b) is carried out immediately following the completion of step (a), and the mixture is allowed to cool to ambient temperature.

Bromination, chlorination and iodination of a reaction product from step (a) is accomplished through methods known by one of ordinary skill in the art. For example, the addition of N-chlorosuccinimide to the mixture of a formula II compound, a silylating agent and an inert organic solvent, results in the conversion of the formula II compound to a C-5 chlorinated compound of formula I.

Similarly, bromination of a formula II compound at the C-5 position is accomplished via the addition of known brominating agents such as elemental bromine, N-bromoacetamide and N-bromosuccinimide. Of these, the use of N-bromosuccinimide is preferred.

Likewise, iodination of a formula II compound at the C-5 position is accomplished by the addition of known iodinating agents such as elemental iodine, iodine monochloride and N-iodosuccinimide. Of these, N-iodosuccinimide is preferred.

Depending upon the desired result, the selected halogenating agent should be added to the mixture in the amount of at least one molar equivalent per mole of substrate.

Step (b) of the process is preferably operated in the absence of light.

The necessary reaction time, for steps (a) and (b), is a function of the starting materials and the operating temperature. The optimum reaction time for a given process is, as always, a compromise which is found by considering the competing goals of throughput, which is favored by short reaction times, and maximum yield, which is favored by long reaction times.

Formula I compounds obtained from the product of this invention are readily isolated by pouring the mixture into water. The product is recovered according to ordinary procedures. For example, the product is collected by filtration, washed with water, dried, reslurried in an organic solvent such as methanol in chloroform, refiltered and redried. The recovered 4-hydroxy-5-halopyrrolo[2,3-d]pyrimidine usually does not need to be further purified for use as an intermediate.

Compounds of formula I are preferably useful as intermediates for preparing novel or known 4-hydroxypyrrolo[2,3-d]pyrimidine-L-glutamic acid derivatives, or for preparing other intermediates which are useful for synthesizing such L-glutamic acid derivatives.

This use of formula I compounds is known in the art. For example, formula I compounds wherein R is hydrogen or alkyl of 1 to 4 carbon atoms are used to prepare N-(pyrrolo[2,3 d]pyrimidin-3-ylacyl)-glutamic acid derivatives which are useful intermediates or final compounds (Taylor, U.S. Pat. No. 4,996,206). Formula I compounds may also be useful for the preparation of pyrrolo[2,3-d]pyrimidine derivatives taught by Akimoto in U.S. Pat. Nos. 4,997,838 and 5,106,974. However, the use of formula I compounds prepared via the processes of this invention are not limited by these examples of such uses.

The following examples further illustrate the processes according to the present invention. The examples are not intended to be limiting to the scope of the invention, in any respect, and should not be so construed.

EXAMPLE 1

2-Amino-4-hydroxypyrrolo[2,3-d]pyrimidine

A mixture of 136.7 g of bromoacetaldehyde diethylacetal, 347 mL of water, and 17.3 mL of concentrated HCl was heated to about 90° C. with vigorous stirring for about 30 minutes, at which time a clear solution was obtained. The solution was cooled to room temperature and 68.3 g of NaOAc was added. The resulting solution was added, with stirring, to a suspension of 100 g of 2,4-diamino-6-hydroxypyrimidine and 34.2 g of NaOAc in 739 mL of water, which had been heated to 70°-85° C. The reaction was allowed to proceed for 2 hours at 70°-85° C., at which time the reaction was complete. The mixture was cooled to 0° C. and held for about 1.5 hours. The mixture was then filtered and the collected product was washed with 500 mL of water and 500 mL of acetone, and dried, affording 72.3 g (79%) of 2-amino-4-hydroxypyrrolo[2,3-d]pyrimidine. A small sample was further purified by slurry in hot methanol, filtration, and drying, mp>300° C. $^1$H NMR (300 MHz, DMSO-d$_6$) $\delta$6.03 (s, 2 H), 6.13 (m, 1 H), 6.56 (dd, J=3.3, 2.3 Hz, 1 H), 10.23 (bs, 1 H), 10.93 (bs, 1 H).

EXAMPLE 2

2-(2,2-Dimethylpropionyl)amino-4-hydroxypyrrolo[2,3-d]pyrimidine 50 g of the 2-amino-4-hydroxypyrrolo[2,3-d]pyrimidine obtained from Example 1 was suspended in 225 mL of toluene, and the toluene was distilled until no further water separated. To the mixture was added 182.8 g of pivalic anhydride and 1.82 g of 4 dimethylaminopyridine. The temperature was increased to 140°-145° C., and residual toluene was removed by distillation. After about 8 hours, when the reaction was complete as indicated by HPLC analysis (acetonitrile—1% aq. HOAc 3:7, C$_{18}$ column, detection at 254 nm, flow rate 2.0 mL/min) the reaction mixture was cooled to room temperature. t-Butylmethyl ether (TBME) was then added to precipitate the product, and the mixture was allowed to slowly cool to about −5° C. and filtered. The wet cake was reslurried with TBME, filtered, and dried in vacuo at 45°-50° C. The product thus obtained was slurried with 1N HCl - DMF 9:1, filtered and dried, affording 45.7 g (65%), of 2-(2,2-dimethylpropionyl)amino-4-hydroxypyrrolo[2,3-d]pyrimidine, mp 296°-301° C. (dec). $^1$H NMR (300 MHz, DMSO-d$_6$) $\delta$1.19 (s, 9 H), 6.36 (dd, J=1.8, 3.2 Hz, 1 H), 6.91 (dd, J=2.2, 3.2 Hz, 1 H), 10.76 (bs, 1 H), 11.54 (bs, 1 H).

EXAMPLE 3

4-Hydroxy-5-iodopyrrolo[2,3-d]pyrimidine

To a solution of 1.0 g of 4-hydroxypyrrolo [2,3-d]pyrimidine in 20 ml of DMF, 3.3 g (2.2 eq) of bis(-trimethylsilyl)acetamide was added, and the resulting solution was stirred at 40° C. in an oil bath for about 2 h. Completeness of silylation was indicated by NMR analysis of an aliquot showing disappearance of the N-3 proton signal. The reaction was cooled to ambient temperature and 1.6 g (1.2 eq) of N-iodosuccinimide (NIS), was added in one portion. The reaction mixture was protected from light and stirred at ambient temperature until completion was indicated by NMR analysis (disappearance of pyrrole C-H doublets and emergence of a single, finely split doublet at $\delta$7.17, about 2 h). The mixture was poured into 50 mL of water with stirring. After 1-2 hours, the product was collected by filtration, washed with water, dried, and reslurried in 10 volumes of 10% methanol in chloroform. Filtration and drying gave 1.7 g of 4-hydroxy-5-iodopyrrolo[2,3-d]pyrimidine (88% yield), mp 248°-253° C. (dec). $^1$H NMR (300 MHz, DMSO-d$_6$) $\delta$7.17 (d, J=2.4 Hz, 1 H), 7.80 (d, J=2.3 Hz, 1 H), 11.82 (s, 1 H), 12.14 (s, 1 H). $^{13}$C NMR (75.5 MHz, DMSO-d$_6$) $\delta$53.8, 107.3, 125.5, 143.6, 147.9, 157.8. Anal. Calcd for C$_6$H$_4$IN$_3$O: C, 27.61; H, 1.54; N, 16.10. Found: C, 27.71; H, 1.48; N, 15.85.

By following the procedures described in Example 3, and employing the appropriate reactants, Examples 4 and 5 were prepared.

EXAMPLE 4

2-Methyl-4-hydroxy-5-iodopyrrolo[2,3-d]pyrimidine

Yield of the title compound was 87%, mp 270°-275° C. (dec). $^1$H NMR (300 MHz, DMSO-d$_6$) $\delta$2.23 (s, 3 H), 7.08 (d, J=2.2 Hz, 1 H), 11.74 s, 1 H), 11.93 s, 1 H). $^{13}$C NMR (75.5 MHz, DMSO-d$_6$) δ20.8, 53.6, 105.0, 124.8, 148.6, 153.1, 158.6. Anal. Calcd for C$_7$H$_6$IN$_3$O: C, 30.57; H, 2.20; N, 15.28. Found: C, 30.30; H, 2.16; N, 14.99.

EXAMPLE 5

2-(2,2-Dimethylpropionyl)amino-4-hydroxy-5-iodopyrrolo[2,3-d]pyrimidine

Yield of the title compound was 72%, mp 255°-260° C. (dec). $^1$H NMR (300 MHz, DMSO-d$_6$) δ1.20 (s, 9 H), 7.07 (d, J=2.0 Hz, 1 H), 10.65 (s, 1 H), 11.74 (s, 1 H), 11.79 (s, 1 H). $^{13}$C NMR (75.5 MHz, DMSO-d$_6$) δ26.3, 39.7, 54.1, 103.8, 125.0, 146.9, 147.9, 156.5, 180.9. Anal. Calcd for C$_{11}$H$_{13}$IN$_4$O$_2$: C, 36.68; H,3.64; N, 15.56. Found: C, 37.14; H, 3.63; N, 15.53.

EXAMPLE 6

4-Hydroxy-5-bromopyrrolo[2,3-d]pyrimidine

To a solution of 1.0 g of 4-hydroxypyrrolo[2,3-d]pyrimidine in 20 ml of DMF, 3.8 g (2.5 eq) of bis(-trimethylsilyl)acetamide was added, and the resulting solution was stirred at 40° C. in an oil bath for about two hours. Completeness of silylation was indicated by NMR analysis of an aliquot showing disappearance of the N-3 proton signal. The reaction was cooled to ambient temperature and 1.6 g (1.2 eq) of N-bromosuccinimide (NBS), was added in one portion. The reaction mixture was protected from light and stirred at ambient temperature until completion was indicated by NMR analysis (disappearance of pyrrole C-H doublets and emergence of a single, finely split doublet at δ7.16, about 2 h). The mixture was poured into 50 mL of water, with stirring. After 1-2 hours, the product was collected by filtration, washed with water, dried, and reslurried in 10 volumes of 10% methanol in chloroform. Filtration and drying gave 1.2 g of 4-hydroxy-5-bromopyrrolo-[2,3-d]pyrimidine (75% yield), mp 269-°271° C. (dec). $^1$H NMR (300 MHz, DMSO-d$_6$) δ7.16 (d, J=2.0 Hz, 1 H), 7.80 (d, J=2.1 Hz, 1 H), 11.87 (s, 1 H), 12.15 (s, 1 H). $^{13}$C NMR (75.5 MHz, DMSO-d$_6$) 89.3, 105.5, 120.4, 144.3, 147.4, 157.5.

By following the procedures described in Example 6, and employing the appropriate reactants, Examples 7 and 8 were prepared.

EXAMPLE 7

2-Methyl-4-hydroxy-5-bromopyrrolo[2,3-d]pyrimidine

Yield of the title compound was 84%, mp 300°-305° C. (dec). $^1$H NMR (300 MHz, DMSO-d$_6$) δ2.23 (s, 3 H), 7.07 (d, J=2.1 Hz, 1 H), 11.77 (S, 1 H), 11.91 (s, 1 H). $^{13}$C NMR (75.5 MHz, DMSO-d$_6$) δ20.8, 89.1, 103.2, 119.6, 148.1, 153.5, 158.2. HRMS m/z (M+) calcd for C$_7$H$_6$BrN$_3$O: 227.9773. Found: 227.9789.

EXAMPLE 8

2-(2,2-Dimethylpropionyl)amino-4-hydroxy-5-bromopyrrolo[2,3-d]pyrimidine

Yield of the title compound was 59%, mp 277°-281° C. (dec). $^1$H NMR (300 MHz, DMSO-d$_6$) δ1.18 (s, 9 H), 7.09 (d, J=2.5 Hz, 1 H), 10.82 (s, 1 H), 11.82 (s, 1 H), 11.87 (s, 1 H). $^{13}$C NMR (75.5 MHz, DMSO-d$_6$) 26.3, 39.7, 89.5, 101.9, 119.6, 147.1, 147.3, 156.0, 180.9. Anal. Calcd for C$_{11}$H$_{13}$BrN$_4$O$_2$: C, 42.19; H, 4.18; N, 17.89. Found: C, 41.77; H, 4.10; N, 17.58.

We claim:

1. A process for preparing 4-hydroxy-5-halopyrrolo[2,3-d]pyrimidines of the formula

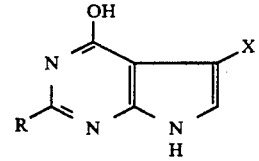

wherein
R is H, C$_1$-C$_4$ alkyl, C$_1$-C$_4$ alkoxy, aryl, benzyl, or a substituent of the formula R$^1$—NH—;
R$^1$ is an amino protecting group; and
X is bromo, chloro or iodo, which comprises
(a) reacting a silylating agent with a 4-hydroxypyrrolo[2,3-d]pyrimidine of the formula

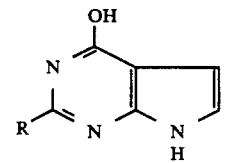

wherein R is as defined above, in the presence of an inert organic solvent; and
(b) iodinating, brominating or chlorinating the reaction product from step (a).

2. A process according to claim 1 wherein at least two molar equivalents of said silylating agent is used in said reaction.

3. A process according to claim 2 wherein said silylating agent is bis(trimethylsilyl)acetamide.

4. A process according to claim 3 wherein said inert organic solvent is N,N-dimethylformamide.

5. A process according to claim 4 wherein said iodinating is accomplished by using N-iodosuccinimide.

6. A process according to claim 4 wherein said brominating is accomplished by using N-bromosuccinimide.

7. A process according to claim 2 wherein R is H.

8. A process according to claim 5 wherein R is H.

9. A process according to claim 6 wherein R is H.

10. A process according to claim 2 wherein R is methyl.

11. A process according to claim 5 wherein R is methyl.

12. A process according to claim 6 wherein R is methyl.

13. A process according to claim 2 wherein R is R$^1$—NH—; and R$^1$ is alkanoyl.

14. A process according to claim 13 wherein R$^1$ is 2,2-dimethylpropionyl.

15. A process according to claim 5 wherein R is R$^1$—NH—; and R$^1$ is alkanoyl.

16. A process according to claim 15 wherein R$^1$ is 2,2-dimethylpropionyl.

17. A process according to claim 6 wherein R is R$^1$—NH—; and R$^1$ is alkanoyl.

18. A process according to claim 17 wherein R$^1$ is 2,2-dimethylpropionyl.

19. In the process for preparing 4-hydroxy-5-halopyrrolo[2,3-d]pyrimidines of the formula

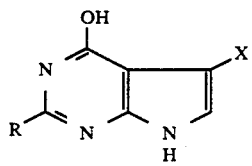

wherein
R is H, $C_1$-$C_4$ alkyl, $C_1$-$C_4$ alkoxy, aryl, benzyl, or a substituent of the formula $R^1$—NH—;
$R^1$ is an amino protecting group; and
X is bromo, chloro or iodo, the improvement which comprises (a) reacting a silylating agent with a 4-pyrrolo[2,3-d]pyrimidine of the formula

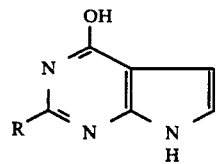

wherein R is as defined above, in the presence of an inert organic solvent; and
(b) iodinating, brominating or chlorinating the reaction product from step (a).

* * * * *

UNITED STATES PATENT AND TRADEMARK OFFICE
CERTIFICATE OF CORRECTION

PATENT NO. : 5,235,053

DATED : August 10, 1993

INVENTOR(S) : Charles J. Barnett and Michael E. Kobierski

It is certified that an error appears in the above-identified patent and that said Letters Patent is hereby corrected as shown below:

On the title page:
Title page, second line of title, "HALOPYRROLD" is misspelled; should be "HALOPYRROLO".

Col. 1, line 11, "inter alia" should be italicized.

Col. 1, line 49, "et al.", should be italicized.

Col. 2, line 35, insert a space between "....2,3-d]" and "intermediates".

Col. 2, line 36, insert "inter alia" between "useful" and "as".

Col. 3, line 44, "131" should be italicized.

Col. 3, line 48, "26" should be italicized.

Col. 3, line 62, "infra" should be italicized.

Col. 3, line 64, "infra" should be italicized.

Col. 4, line 5, insert "d]" before "pyrimidine".

Col. 4, line 9, "in situ" should be italicized.

Col. 4, line 31, "dimethylformide" is misspelled; should be "dimethylformamide".

Col. 6, line 10, "d]pyrimidine" should be adjacent to "rolo[2,3-"" on line 8.

Col. 6, line 26, "in vacuo" should be italicized.

UNITED STATES PATENT AND TRADEMARK OFFICE
CERTIFICATE OF CORRECTION

PATENT NO. : 5,235,053

DATED : August 10, 1993

INVENTOR(S) : Charles J. Barnett and Michael E. Kobierski

It is certified that an error appears in the above-identified patent and that said Letters Patent is hereby corrected as shown below:

Col. 7, line 1, insert "(" before "s, 1 H)" (two instances, same line).

Col. 7, line 15, insert space between "H" and "3.64".

Col. 7, line 39, delete "-" between "o" and "[" in "bromopyrrolo-[2,3-d]....".

Col. 7, line 43, insert "δ" before "89.3".

Col. 7, lne 53, "(S, 1 H)" should read "(s, 1 H)".

Col. 7, line 64, insert "δ" before "26.3".

Col. 10, line 1, "4-pyrrolo[2,3-", should read "4-hydroxypyrrolo[2,3-".

Signed and Sealed this

Tenth Day of May, 1994

BRUCE LEHMAN

Attest:

Attesting Officer

Commissioner of Patents and Trademarks